United States Patent
Allison et al.

(10) Patent No.: US 9,352,060 B2
(45) Date of Patent: May 31, 2016

(54) CARRAGEENAN GEL AIR FRESHENER

(75) Inventors: Gerald Allison, Plainsboro, NJ (US);
Nicholas O'Leary, Plainsboro, NJ (US)

(73) Assignee: Firmenich SA, Geneva (CH)

( * ) Notice: Subject to any disclaimer, the term of this patent is extended or adjusted under 35 U.S.C. 154(b) by 129 days.

(21) Appl. No.: 14/241,443

(22) PCT Filed: Aug. 27, 2012

(86) PCT No.: PCT/EP2012/066604
§ 371 (c)(1),
(2), (4) Date: Feb. 26, 2014

(87) PCT Pub. No.: WO2013/030153
PCT Pub. Date: Mar. 7, 2013

(65) Prior Publication Data
US 2014/0371129 A1    Dec. 18, 2014

Related U.S. Application Data

(60) Provisional application No. 61/529,393, filed on Aug. 31, 2011.

(30) Foreign Application Priority Data

Sep. 27, 2011   (EP) ..................................... 11182842

(51) Int. Cl.
*A61L 9/012*   (2006.01)
*A61L 9/04*   (2006.01)

(52) U.S. Cl.
CPC . *A61L 9/012* (2013.01); *A61L 9/048* (2013.01)

(58) Field of Classification Search
CPC ................................. A61L 9/012; A61L 9/048
USPC ............................................................. 512/4
See application file for complete search history.

(56) References Cited

U.S. PATENT DOCUMENTS

| 4,056,612 A | 11/1977 | Lin |
| 5,741,482 A * | 4/1998 | Modi ............................ 424/76.3 |
| 2012/0219520 A1 * | 8/2012 | Allison et al. ............... 424/76.4 |

FOREIGN PATENT DOCUMENTS

| DE | 200 09 445 U1 | 8/2000 |
| WO | WO 2011/067732 A1 | 6/2011 |

OTHER PUBLICATIONS

International Search Report and Written Opinion, application PCT/EP2012/066604, mailed Oct. 26, 2012.

* cited by examiner

*Primary Examiner* — Ling Choi
*Assistant Examiner* — Lanee Reuther
(74) *Attorney, Agent, or Firm* — Winston & Strawn LLP

(57) ABSTRACT

The present invention relates to the field of perfumery. It relates more particularly to a gel device which allows for an effective and prolonged evaporation of an active volatile ingredient. The gel device of the present invention comprises an active volatile and a gelling agent formed of carrageenan together with dibutyl lauroyl glutamide and/or dibutyl ethylhexanoyl glutamide, and a polyol.

19 Claims, No Drawings

CARRAGEENAN GEL AIR FRESHENER

This application is a 371 filing of International Patent Application PCT/EP2012/066604 filed Aug. 27, 2012, which claims the benefit of prior application Nos. U.S. 61/529,393 filed Aug. 31, 2011 and EP 11182842.2 filed Sep. 27, 2011.

TECHNICAL FIELD

The present invention relates to the field of perfumery. It relates more particularly to a gel device which allows for an effective and prolonged evaporation of an active volatile ingredient contained therein. The gel device of the present invention comprises an active volatile and a gelling agent essentially formed of carrageenan, further comprising dibutyl lauroyl glutamide and/or dibutyl ethylhexanoyl glutamide, together with a polyol.

PRIOR ART

The use of various devices for the diffusion of volatile compounds, for example perfumes, sanitizing agents, insect repellents and the like, has become more and more current in recent years. Air-freshening devices or deodorizers are currently used in practically all households to mask bad odors or to diffuse fragrances or other volatile active ingredients to the air surrounding the device, in particular in rooms and cupboards, litter containers, and other closed environments.

Amongst the various types of devices that can be used to diffuse fragrances and other air modifying substances such as purifying or sanitizing agents, one class of systems capable of diffusing active volatile ingredients are solid state devices consisting of solid materials or carriers impregnated with an active ingredient. Such devices may be formed of various materials which are capable of absorbing the ingredient and subsequently releasing it in a more or less controlled manner. Examples of such known materials include gels, such as agar-agar or sodium stearate gels, synthetic polymer resins, or blocks of mineral material, e.g. plaster or silica.

The present invention relates to a device formed of such materials capable of absorbing the active substance and more particularly to a gel device formed of an absorbing material selected from the so-called superabsorbent polymers such as starch based systems, chemically modified cellulose and natural gums. These are typically hydrogels which can be divided into two classes: nonionic and ionic polymers. Amongst the ionic polymers there are hydrocolloidal polysaccharides based on naturally occurring polysaccharides, such as carrageenan, sodium carboxymethyl cellulose, sodium alginate, pectins, xanthan and guar gum, all of which have been considered in the context of the present invention.

The invention relates more particularly to an improved carrageenan type gel. Carrageenan gels are commonly used for the diffusion of volatile substances but their performance with regard to the diffusion of the volatile active substance is not always ideal as a consequence of their tight matrix. Such gels traditionally comprise a certain amount of hydrophilic components, namely water, which act as an evaporation aid for the active volatile ingredients. However, with water the moisture release occurs very rapidly, and the outer layer of these conventional gels tends to dry quickly, creating an occlusive barrier to the evaporation of the volatiles. As a result, the volatiles are entrapped within the core of the gel, and their release is hindered after some time following their exposure to air, which leads to poor olfactive performance of the product.

It is therefore still desirable to provide carrageenan based gels with improved properties, in particular a more linear release of the volatile active substance, namely a fragrance, from the carrageenan gel matrix. In order to ensure a regular and prolonged activity of the gel, limiting exudation or syneresis of the volatiles out of the gel is also advantageous.

The present invention brings a novel solution to the above problems by providing carrageenan based gels with significant improvement in fragrance durability and impact.

DESCRIPTION OF THE INVENTION

The present invention relates to a gel susceptible of enclosing a volatile active ingredient within and of permitting the diffusion of said volatile ingredient from the gel upon exposure of the latter to air.

The invention also relates to a method for the diffusion of the active volatile substances into ambient air, in particular air in closed spaces, the method comprising exposing a gel such as described above to ambient air, under conditions making it possible to diffuse the active volatile substance.

We have found that the diffusion systems according to the invention provide a very uniform and prolonged diffusion of the active ingredient.

The gels according to the invention are intended for the diffusion of an active volatile ingredient and comprise:
   a) an oil containing said active volatile ingredient;
   b) a gelling agent formed of a carrageenan gelling component together with dibutyl lauroyl glutamide and/or dibutyl ethylhexanoyl glutamide; and
   c) a polyol plasticizer.

Following a particular embodiment of the gels of the invention, the gel consists of the ingredients a) to c) as defined above, meaning that it is essentially formed of these three components and only contains minimal amounts of other ingredients, the total concentration of which, in the gel, is not above 2% by weight, relative to the total weight of the gel.

As active ingredient in all gels, there can be used for example a perfume. Other suitable active ingredients comprise deodorizing or sanitizing agents, or insect repellents, or yet any other volatile materials capable of imparting perceptible and desirable benefits to the quality of the air into which they are diffused. In particular, it is also advantageous to use volatile ingredients that are capable of neutralizing or masking bad odors, i.e. malodor counteracting ingredients.

In all embodiments of the invention, the active ingredient absorbing material according is essentially formed of carrageenan gel. The latter is preferably present in the final gel in an amount of from 0.5 to 2.5 weight %, relative to the total weight of the gel. As the carrageenan material, there can be used any commercially available carrageenan such as for example the substances sold under the commercial tradename of Gelcarin® AF7810 from FMC Biopolymer. The latter are powder materials that can be admixed with water or another appropriate hydrophilic medium to form the gel, in a generally known manner.

According to the invention, best results were obtained when the carrageenan material was selected from the group consisting of kappa-carrageenan, iota-carrageenan and mixtures thereof.

As additional gelling agents in the gels of the invention, there are used the amino acids dibutyl lauroyl glutamide, dibutyl ethylhexanonyl glutamide or mixtures thereof. Preferred embodiments of the invention contain mixtures of the two.

Dibutyl lauroyl glutamide and dibutyl ethylhexanoyl glutamide are both available commercially. For example, dibutyl lauroyl glutamide can be obtained under the tradename GP-1 from Ajinomoto Co, Tokyo, Japan. Dibutyl ethylhexanoyl glutamide can be obtained from the same company, under the tradename EB-21.

The total amount of dibutyl lauroyl glutamide and dibutyl ethylhexanoyl glutamide present in the gels of the invention is preferably from 0.005 to 1.0% by weight, even more preferably from 0.01 to 0.2% by weight, relative to the total weight of the gel.

Dibutyl lauroyl glutamide and dibutyl ethylhexanoyl glutamide are preferably present in concentrations ranging from 0.0025 to 0.2 weight % each, said percentages being defined relative to the total weight of the gel.

The use of other amino acids/proteins, especially water soluble variants, can also positively affect the physical properties of the gel, such as tensile strength and, as a result diminish the syneresis generally associated with these carrageenan based hydrogels, hence positively affecting fragrance performance.

As the plasticizer in any embodiment of the invention's gels, there is used a polyol. Suitable polyols include polyethylene glycols, polypropylene glycols, trimethylol propane, glycerine, sorbitols, as well as any appropriate mixture thereof. Preferably, the plasticizer will be a polyethylene glycol or a mixture of polyethylene glycols. As the latter, commercially available materials of varied molecular weight can be used. For example, commercial products such as polyethylene glycol 1000 (known as Carbowax®, from Dow Chemical) are perfectly appropriate for the purposes of the invention. Other lower molecular weight products such as PEG 300, PEG 400, or yet PEG 600 (all commercially available from Dow Chemical), also showed good physical compatibility with the gels according to the invention. When the gel according to the invention is used for the diffusion of a fragrance, it is preferred to use a polyethylene glycol, or a mixture of polyethylene glycols, the molecular weight of which is not above 1000 g/mol, to avoid a negative impact on the olfative quality of the diffused fragrance. Polyethylene glycol 1000 proved to provide the most advantageous gels according to the invention.

The plasticizer ingredient will be present in the gels in a concentration of from 0.5 to 30% by weight, relative to the total weight of gel. More preferred amounts vary from 4 to 15% by weight, or even from 6 to 12% by weight, relative to the weight of the gel, with concentrations around 10% by weight providing excellent results as illustrated in the examples presented further on.

The third component in the gels of the invention is the "active volatile ingredient" by which it is meant here an individual ingredient, as well as a mixture of active volatile ingredients.

The active volatile ingredient is preferably selected from a perfume or a malodor counteractant, but it may also be a bactericide, an insecticide, an insect- or animal-repellent or attractant. Typically, mixtures of such ingredients can also be used.

As "perfume" one may use any perfuming ingredient or a mixture thereof. A "perfuming ingredient" is meant here as a compound which is of current use in the perfumery industry, i.e. a compound which is used as active ingredient in perfuming compositions or in perfumed products in order to impart a hedonic effect into its surroundings. In other words, such an ingredient or mixture, to be considered as being a perfuming one, must be recognized by a person skilled in the art of perfumery as being able to impart or modify, preferably in a positive or pleasant way, the odor of a composition or product, and not just as having an odor. Moreover, this definition is also meant to include compounds that do not necessarily have an odor but are capable of modulating the odor of a perfuming composition or of a perfumed product and, as a result, of modifying the perception by a user of the odor of such a composition or product.

The nature and type of these perfuming ingredients do not warrant a more detailed description here, which in any case would not be exhaustive, the skilled person being able to select them on the basis of his general knowledge, the intended use or application and the desired organoleptic effect. In general terms, these perfuming ingredients belong to chemical classes as varied as alcohols, aldehydes, ketones, esters, ethers, acetates, nitriles, terpene hydrocarbons, nitrogenous or sulphurous heterocyclic compounds and essential oils. Said perfuming ingredients can be of natural or synthetic origin. Many of these ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

By the term "malodor counteractant" or "malodor counteracting ingredient" we mean here compounds which are capable of reducing the perception of malodor, i.e. of an odor that is unpleasant or offensive to the human nose, by counteracting and/or masking malodors. In particular embodiments, these compounds have the ability to react with key compounds which are known or suspected to be the cause of the malodor. The reactions result in reduction of the malodor materials' airborne levels and consequent reduction in the perception of the malodor.

Preferably, the active volatile is a perfume or a malodor counteractant. The gel device of the present invention is then preferably an air-freshener.

Typically, the perfume may also contain a carrier of current use in perfumery such as a solvent. The amount and nature of such current perfume additives can be selected and its amount adjusted by the skilled person so as to not adversely affect the properties of the gel according to the invention. Perfume ingredients or mixtures of ingredients may also be carried in an encapsulated form, enclosed in encapsulating carriers of current use in perfumery. Fragrance microcapsules may be advantageous to protect particularly fragile perfuming ingredients, or yet to delay the release of certain perfume components and thus create a slow release impact. The same applies when so-called pro-fragrances (i.e. chemical substances of high molecular weight, generally not odorant as such but able to generate an odorant by chemical or photochemical reaction under use conditions) are used according to the invention.

The active volatile can be dissolved in any suitable solvent.

The active volatile ingredient may also contain an insect repellent. Non-limiting examples of suitable insect repellents include citronella, dimethyl phthalate and n,n-dimethyl-m-tolumide, but any other insect repellent agent can be used according to the invention.

In all embodiments of the invention, the amount of active volatile ingredient or mixture of ingredients shall be from 0.5 to 2.0% by weight, and more preferably from 1.0 to 2.0% by weight of active volatile ingredient, relative to the total weight of the gel.

The gel of the present invention may also optionally include one or more additional components so to provide enhanced or additional aesthetic and/or functional improvements thereto. In particular, the additional materials that may be included in the gel device include antibacterial agents, coloring agents, decorative materials, stabilizers, antioxidants, and UV blockers. Another optional but useful component is an indicator which helps the consumer assert when the active volatile ingredient is no longer present in the gel (fragrance exhausted, no longer diffused), i.e. an end point indicator.

Generally, as cited above, the total amount of such optional ingredients in the gels of the invention shall not be above 2% by weight, relative to the total weight of the gel.

These optional ingredients do not warrant a more detailed description here, which would in any case not be exhaustive. The skilled person is capable of selecting them on the basis of general knowledge in the art and the desired characteristics of the gel device. In particular, the kind and amount of the additional ingredients are selected in a manner ensuring that the rigidity and other desirable properties of the gel are not affected.

In another aspect, the invention provides a process for the preparation of a gel for the diffusion of an active volatile ingredient, wherein there is used a gelling agent formed of carrageenan together with dibutyl lauroyl glutamide and/or dibutyl ethylhexanoyl glutamide, and a plasticizer as previously defined. The gels can be prepared by simply mixing these ingredients in the appropriate proportions and at an appropriate temperature, and kneading the mixture until the gel is perfectly homogeneous.

In a preferred embodiment of this preparation process, the latter comprises the following steps:
  a) the carrageenan gel phase is prepared by dissolving an appropriate amount of carrageenan powder in hot water at a temperature from 60° C. to 70° C. and under stirring until formation of a carrageenan gelling component;
  b) dibutyl lauroyl glutamide and/or dibutyl ethylhexanoyl glutamide are premixed with the plasticizer at a temperature from 60° C. to 70° C. and under stirring to form a uniform mixture;
  c) the carrageenan gelling component and the uniform mixture obtained in step b) are then admixed at a temperature not below 60° C. to form a fluid gel and the latter is allowed to cool to room or ambient temperature to form a solid gel.

Preferably, the temperature at which step c) is carried out is from 60 to 70° C.

Typical concentrations of carrageenan powder to water are from 5:95 to 1:99, respectively, but the skilled person is able to adjust the relative proportions of these two ingredients according to the desired carrageenan gel premix properties.

According to preferred embodiments of this process, the fluid gel obtained in step c) is poured into a mould or suitable container before being allowed to cool down to room temperature (typically 15 to 25° C.). Such embodiments make it possible to obtain solid gels with a determined form and allow the realization of decorative air fresheners and other gel devices. Of course, the gel may also be used as obtained above, without employing a mould or a container.

The active volatile ingredient, preferably a fragrance or malodor counteractant, can be added at several stages of the gel preparation. For example, it may be dispersed in the carrageenan gel mix of step a) before the latter is admixed with the mixture of the amino acid gelling agents and plasticizer obtained in step b). Alternatively, part of the fragrance is added to the carrageenan gel mix and the rest to the mixture prepared in step b), the two being then admixed as recited in step c).

Any optional ingredients that may be added to the gel device of the invention are typically added together with the oily active volatile ingredient.

All embodiments of the gels according to the invention can be prepared according to the above-described process, wherein the use of preferred ingredients and relative proportions thereof, as defined in previous sections of this description, make it possible to obtain a variety of gels with advantageous properties.

The formed gels are characterized by a generally rigid gel structure and are able to stand freely, whilst having some gel matrix flexibility and minimal syneresis. The transfer of the fragrance entrapped therein into the surroundings of the gel is improved and they present a smoother, less rigid-like, surface appearance and improved mobility of water with less pronounced gradients from center to surface, therefore reducing crust formation on the surface of the air freshener.

We have been able to establish that combining the carrageenan gelling component with the amino acid gelling agents cited and the polyol makes it possible to obtain gels sufficiently plasticized, so as to allow an efficient and maximum evaporation of the active volatile ingredients throughout the lifetime of the gel device, resulting in a better performance of the air fresheners.

We have also found that the gel devices of the present invention advantageously provide a very uniform and prolonged diffusion of the active ingredient carried therein. Unlike prior known carrageenan gels, the useful lifetime of which is typically of a couple of weeks, the gels of the present invention show linear diffusion of the fragrance for a period of more than four weeks.

As anticipated above, the composition of the invention can be contained in, or associated with, a consumer article, whereby as a consumer article it is intended here more specifically a volatile material dispenser. Therefore, a consumer article in the form of a volatile material dispenser containing the gel of the invention is also an object of the present invention.

Such a volatile material dispenser can be, depending on the nature of the active volatile used in the preparation of the gel a perfuming or sanitizing device. Non-limiting examples of said volatile material dispenser are an air-freshener, particularly of the solid type, a diaper pail freshener, a car freshener, a closet freshener, a wardrobe air-freshener, a drawer freshener, an animal litter box freshener, a shoe freshener or a garbage pail freshener, an insecticide or an insect repellent device, or a mothproofer.

The preferred consumer article is an air-freshener of the gel type.

In fact, a container and an adequate gel of the invention will compose said consumer article. The gel can be housed in the container or a packaging material. In some embodiments, at least a portion of the container surface is able to allow the release of the vapors of the volatile active component into the air surrounding said consumer article. The container can be made of any material usable for this kind of consumer article. Naturally said material must be chemically inert towards the gel of the invention. Standard packages used for these kinds of articles, such as plastics-polypropylene, polyvinyl chloride, high density polyethylene, P.E.T. and glass, are well suited.

During storage, at least the portion of the container that is able to allow the release of the vapors into the exterior of said contained is sealed, in order not to allow diffusion of the volatile active ingredient, in particular the fragrance, into the storage surroundings. The consumer can then activate the consumer article, namely air freshener, simply by removing the seal, after which the fragrance will start to diffuse into the surrounding air.

The invention also relates to a process for diffusing an active volatile ingredient into ambient air comprising exposing to air a gel device of the invention. In a preferred embodiment of the invention, the gel device is exposed to air in a closed space such as for example a room, a cupboard, a wardrobe, a drawer, an animal litter box or a garbage container.

The invention will now be described in further detail by way of the following examples wherein the amounts are indicated in % by weight, relative to the weight of the gel, and the temperatures are indicated in degrees centigrade.

Example 1

Preparation of a Gel Device According to the Invention

A gel was prepared by mixing the following ingredients in the amounts indicated.

| Ingredient | Amount (% by weight) |
| --- | --- |
| Perfume oil | 1.00 |
| GP-1[1] | 0.02 |
| EB-21[2] | 0.02 |
| Polyethylene glycol 1000 | 7.96 |
| Carrageenan gel, premix | 91.00 |

[1]Dibutyl lauroyl glutamide, origin: Ajinomoto Co., Tokyo, Japan
[2]Dibutyl ethylhexanoyl glutamide, origin: Ajinomoto Co., Tokyo, Japan The carrageenan gel cited in the table above was prior prepared by slowly admixing carrageenan powder in water (2.0% Carrageenan powder, water 97.8%, preservative 0.2% w/w) at 70° C. The solution was then heated to about 80 to 95° C. and stirred until a uniform gel was obtained.

GP-1 and EB-21 were premixed and added of the polyethylene glycol 1000 and heated to around 65° C., under stirring and the fragrance was added thereto.

Finally, the carrageenan gel and the mixture of amino acids, polyethylene glycol and fragrance were mixed under stirring until obtaining a fluid gel that was then poured into an appropriate container and cooled to room temperature.

Example 2

Preparation of a Gel Device According to the Invention

The process described in Example 1 was repeated, using the ingredients in the table below, in the proportions indicated.

| Ingredient | Amount (% by weight) |
| --- | --- |
| Perfume oil | 1.00 |
| GP-1[1] | 0.08 |
| EB-21[2] | 0.08 |
| Polyethylene glycol 1000 | 8.00 |
| Carrageenan gel, premix | 90.84 |

[1]Dibutyl lauroyl glutamide, origin: Ajinomoto Co., Tokyo, Japan
[2]Dibutyl ethylhexanoyl glutamide, origin: Ajinomoto Co., Tokyo, Japan Example 3

Preparation of a Gel Device According to the Invention

The process described in Example 1 was repeated, using the ingredients in the table below, in the proportions indicated.

| Ingredient | Amount (% by weight) |
| --- | --- |
| Perfume oil | 1.00 |
| GP-1[1] | 0.04 |
| Polyethylene glycol 1000 | 4.96 |
| Carrageenan gel, PREMIX | 94.00 |

[1]Dibutyl lauroyl glutamide, origin: Ajinomoto Co., Tokyo, Japan

Example 4

Preparation of a Gel Device According to the Invention

The process described in Example 1 was repeated, using the ingredients in the table below, in the proportions indicated.

| Ingredient | Amount (% by weight) |
| --- | --- |
| Perfume oil | 1.00 |
| GP-1[1] | 0.04 |
| EB-21[2] | 0.01 |
| Polyethylene glycol 1000 | 9.95 |
| Carrageenan gel | 89.00 |

[1]Dibutyl lauroyl glutamide, origin: Ajinomoto Co., Tokyo, Japan
[2]Dibutyl ethylhexanoyl glutamide, origin: Ajinomoto Co., Tokyo, Japan Example 5

Preparation of a Gel Device According to the Invention

The process described in Example 1 was repeated, using the ingredients in the table below, in the proportions indicated.

| Ingredient | Amount (% by weight) |
| --- | --- |
| Perfume oil | 1.00 |
| GP-1[1] | 0.20 |
| EB-21[2] | 0.20 |
| Polyethylene glycol 1000 | 10.00 |
| Carrageenan gel, premix | 88.60 |

[1]Dibutyl lauroyl glutamide, origin: Ajinomoto Co., Tokyo, Japan
[2]Dibutyl ethylhexanoyl glutamide, origin: Ajinomoto Co., Tokyo, Japan

What is claimed is:
1. A gel for the diffusion of an active volatile ingredient comprising:
   a) an oil containing said active volatile ingredient;
   b) a gelling agent formed of carrageenan gelling component together with dibutyl lauroyl glutamide and/or dibutyl ethylhexanoyl glutamide; and
   c) a polyol plasticizer.

2. A gel for the diffusion of an active volatile ingredient consisting of:
   a) an oil containing said active volatile ingredient;
   b) a gelling agent formed of carrageenan gelling component together with one of dibutyl lauroyl glutamide or dibutyl ethylhexanoyl glutamide; and
   c) a polyol plasticizer.

3. A gel according to claim 2, wherein the carrageenan is present in an amount of 0.5 to 2.5 weight %, relative to the total weight of the gel and the dibutyl lauroyl glutamide or dibutyl ethylhexanoyl glutamide is present in an amount of from 0.005 to 1% by weight, relative to the total weight of the gel.

4. A gel according to claim 3, wherein the dibutyl lauroyl glutamide or dibutyl ethylhexanoyl glutamide is present in an amount of from 0.0025 to 0.2 weight %, relative to the total weight of the gel.

5. A gel according to claim 2, wherein the carrageenan material is selected from the group consisting of kappa-carrageenan, iota-carrageenan and mixtures thereof.

6. A gel according to claim 2 wherein the polyol plasticizer is a polyethylene glycol.

7. A gel according to claim 2, in the form of an air freshener.

8. A gel according to claim 1, comprising carrageenan in an amount of 0.5 to 2.5 weight %, relative to the total weight of the gel.

9. A gel according to claim 1, wherein dibutyl lauroyl glutamide and dibutyl ethylhexanoyl glutamide, taken together, are present in an amount of from 0.005 to 1% by weight, relative to the total weight of the gel.

10. A gel according to claim 9, wherein each of dibutyl lauroyl glutamide and/or dibutyl ethylhexanoyl glutamide is present in an amount of from 0.0025 to 0.2 weight %, relative to the total weight of the gel.

11. A gel according to claim 1, wherein the carrageenan material is selected from the group consisting of kappa-carrageenan, iota-carrageenan and mixtures thereof.

12. A gel according to claim 1 wherein the polyol plasticizer is a polyethylene glycol.

13. A gel according to claim 1, wherein the active volatile is a perfume or a malodor counteractant.

14. A gel according to claim 1, in the form of an air freshener.

15. A process for the preparation of a gel as defined in claim 1, which comprises the following steps:
   a) preparing a carrageenan gel phase by dissolving an appropriate amount of carrageenan powder in hot water at a temperature from 60 to 70° C. and under stifling until formation of a carrageenan gelling component;
   b) premixing dibutyl lauroyl glutamide and/or dibutyl ethylhexanoyl glutamide with the plasticizer at a temperature from 60 to 70° C. and under stifling to form a uniform mixture;
   c) admixing the carrageenan gelling component and the uniform mixture obtained in step b) at a temperature not below 60° C. to form a fluid gel and allowing the latter to cool down to room or ambient temperature to form a solid gel.

16. A process according to claim 15, further comprising pouring the fluid gel prepared in step c) into a suitable container, before cooling.

17. A process according to claim 1, wherein step c) is carried out at a temperature from 60 to 80° C.

18. A process for diffusing an active volatile ingredient into ambient air, comprising exposing to air a gel according to claim 1.

19. A process according to claim 18, wherein the gel is exposed to air in a closed space.

* * * * *

UNITED STATES PATENT AND TRADEMARK OFFICE
CERTIFICATE OF CORRECTION

PATENT NO.        : 9,352,060 B2
APPLICATION NO.   : 14/241443
DATED             : May 31, 2016
INVENTOR(S)       : Allison et al.

It is certified that error appears in the above-identified patent and that said Letters Patent is hereby corrected as shown below:

In the Claims

Column 10:
Line 13 (claim 15, line 5), after "at a temperature from 60 to 70° C. and under", change "stifling" to -- stirring --.
Line 17 (claim 15, line 9), after "ture from 60 to 70° C. and under", change "stifling" to -- stirring --.

Signed and Sealed this
Second Day of August, 2016

Michelle K. Lee
*Director of the United States Patent and Trademark Office*